(12) United States Patent
Oda et al.

(10) Patent No.: US 10,398,745 B2
(45) Date of Patent: Sep. 3, 2019

(54) AGENT FOR REDUCING THE NUMBER OF INTESTINAL BACTERIA, FOOD, AND PHARMACEUTICAL PRODUCT

(71) Applicant: FUJIFILM Corporation, Tokyo (JP)

(72) Inventors: Yuriko Oda, Ashigarakami-gun (JP); Fumitaka Ueda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/415,006

(22) Filed: Jan. 25, 2017

(65) Prior Publication Data
US 2017/0209509 A1 Jul. 27, 2017

(30) Foreign Application Priority Data

Jan. 26, 2016 (JP) ................. 2016-012252

(51) Int. Cl.
*A61K 36/37* (2006.01)

(52) U.S. Cl.
CPC .......... *A61K 36/37* (2013.01); *A61K 2236/15* (2013.01); *A61K 2236/331* (2013.01); *A61K 2236/51* (2013.01)

(58) Field of Classification Search
None
See application file for complete search history.

(56) References Cited

U.S. PATENT DOCUMENTS

| 9,616,066 | B2 * | 4/2017 | Lamb .................. A61K 31/365 |
| 2013/0189745 | A1 | 7/2013 | Schwarz et al. |
| 2014/0255351 | A1 | 9/2014 | Berstad et al. |
| 2015/0030690 | A1 | 1/2015 | Mercati et al. |
| 2015/0132338 | A1 | 5/2015 | Oda et al. |
| 2015/0209383 | A1 | 7/2015 | Boileau et al. |

FOREIGN PATENT DOCUMENTS

| EP | 2 422 813 A1 | 2/2012 |
| JP | 2010-285425 A | 12/2010 |
| JP | 2013-530717 A | 8/2013 |
| JP | 2014-530229 A | 11/2014 |
| JP | 2014-240431 A | 12/2014 |
| JP | 2014-532710 A | 12/2014 |
| JP | 2015-127340 A | 7/2015 |
| WO | WO 2018/011594 A1 * | 1/2018 |

OTHER PUBLICATIONS

Sokol (PNAS (2008), vol. 105, No. 43, pp. 16731-16736).*
Paarakh (Journal of Natural Remedies (2008), vol. 8, No. 2, pp. 116-131).*
Scott K P et al: "Manipulating the gut microbiota to maintain health and treat disease", Microbial Ecology in Health & Disease, vol. 26, 25877, 2015, 10 pgs. total.
New Extended European Search Report dated Sep. 21, 2017, issued by the European Patent Office in corresponding European Application No. 17153019.9.
Extended European Search Report dated May 29, 2017, issued from the European Patent Office in corresponding European Patent Application No. 17153019.9.
Kishino, E. et al., "A mixture of *Salacia reticulata* (Kotala himbutu) aqueous extract and cyclodextrin reduces body weight gain, visceral fat accumulation, and total cholesterol and insulin increases in male Wistar fatty rats", Nutrition Research, Elsevier Inc., vol. 29, No. 1, Jan. 1, 2009, pp. 55-63 (9 pages total).
Communication dated Apr. 5, 2019, from the European Patent Office in counterpart European Application No. 17153019.9.
S. Miquel, et al., "*Faecalibacterium prausnitzii* and human intestinal health", Current Opinion in Microbiology, vol. 16, No. 3, Jun. 1, 2013, pp. 255-261 (7 pages total).
Chika Kasai, et al., "Comparison of the gut microbiota composition between obese and non-obese individuals in a Japanese population, as analyzed by terminal restriction fragment length polymorphism and next-generation sequencing", BMC Gastroenterology, Biomed Central Ltd., London, GB, vol. 15, No. 1, Aug. 11, 2015 (10 pages total, labeled as p. 1 of 10 to p. 10 of 10).
Keishi Kameyama, et al., "Intestinal Colonization by a *Lachnospiraceae* Bacterium Contributes to the Development of Diabetes in Obese Mice", Microbes and Environments, vol. 29, No. 4, Jan. 1, 2014, pp. 427-430 (4 pages total).
Office Action dated Nov. 6, 2018, from Japanese Patent Office in counterpart Japanese Application No. 2017-011312.

* cited by examiner

*Primary Examiner* — Susan Hoffman
(74) *Attorney, Agent, or Firm* — Sughrue Mion, PLLC

(57) ABSTRACT

The present invention provides an agent for suppressing the number of intestinal bacteria, which contains an extract and/or crushed product of a plant of the genus *Salacia*, wherein the intestinal bacterium is at least one which is selected from the group consisting of the families Lachnospiraceae, Ruminococcaceae, Fusobacteriaceae, and Desulfovibrionaceae.

5 Claims, No Drawings

AGENT FOR REDUCING THE NUMBER OF INTESTINAL BACTERIA, FOOD, AND PHARMACEUTICAL PRODUCT

CROSS-REFERENCE TO RELATED APPLICATIONS

The present application claims priority under 35 U.S.C. § 119 to Japanese Patent Application No. 2016-12252 filed on Jan. 26, 2016. The above application is hereby expressly incorporated by reference, in its entirety, into the present application.

TECHNICAL FIELD

The present invention relates to an agent for suppressing the number of intestinal bacteria, which is capable of suppressing the number of particular intestinal bacteria associated with a disease. The present invention further relates to a food and a pharmaceutical product, which contain the agent for suppressing the number of intestinal bacteria.

BACKGROUND ART

Roots and stems of plants of the genus *Salacia* have been used as natural drugs in a traditional medicine called "Ayurveda" in India and Sri Lanka. In Sri Lanka, it is traditionally known that the root bark of *Salacia reticulata* is effective for treatment of rheumatism, gonorrhoea, and skin diseases. Also, the tradition of using the root bark for treatment of early diabetes has been carried on.

It has been revealed that an extract or crushed product of a plant of the genus *Salacia* is effective to change the intestinal flora. For example, Patent Literature 1 discloses an agent for preventing an increase in body weight, which contains an extract of a plant of the genus *Salacia*, wherein the extract of a plant of the genus *Salacia* causes an increase in the proportion of the phylum *Bacteroidetes* and a decrease in the proportion of the phylum *Firmicutes* in the intestinal flora, thereby adjusting the component ratio of the intestinal flora. Patent Literature 2 discloses a method for reducing *Enterobacter* or *Clostridium* bacteria using crushed product or extract of plant of the genus *Salacia* and flavonoids.

CITATION LIST

Patent Literatures

Patent Literature 1: JP Patent Publication (Kokai) No. 2015-127340 A
Patent Literature 2: JP Patent Publication (Kokai) No. 2014-240431 A

SUMMARY OF INVENTION

Technical Problem

Patent Literature 1 and 2 do not disclose the effects on bacteria associated with particular diseases (bacteria of the families Lachnospiraceae, Ruminococcaceae, Fusobacteriaceae, and Desulfovibrionaceae). It is known that particular intestinal bacteria are associated with diseases. However, there is no established method for treating diseases by controlling particular intestinal bacteria. An object of the present invention is to provide an agent for suppressing the number of intestinal bacteria, which is capable of suppressing the number of particular intestinal bacteria associated with a disease. Another object of the present invention is to provide a food and pharmaceutical product containing such agent for suppressing the number of intestinal bacteria.

Means for Solution to Problem

As a result of intensive studies in order to achieve the above objects, the present inventors have confirmed that it is possible to suppress the number of particular intestinal bacteria involved in a disease such as an inflammatory bowel disease using an extract of a plant of the genus *Salacia*, and it is also possible to alleviate symptoms of disease model animals using an extract of a plant of the genus *Salacia*. This has led to the completion of the present invention. According to the present invention, the following inventions are provided.

[1] An agent for suppressing the number of intestinal bacteria, which contains an extract and/or crushed product of a plant of the genus *Salacia*, wherein the intestinal bacterium is at least one which is selected from the group consisting of the families Lachnospiraceae, Ruminococcaceae, Fusobacteriaceae, and Desulfovibrionaceae.

[2] The agent for suppressing the number of intestinal bacteria according to [1], wherein the intestinal bacterium is at least one which is selected from the group consisting of the family Lachnospiracea, the family Ruminococcaceae, the genus *Fusobacterium* of the family Fusobacteriaceae, and the genus *Desulfovibrio* of the family Desulfovibrionaceae.

[3] The agent for suppressing the number of intestinal bacteria according to [1] or [2], wherein the intake or dose of the extract and/or crushed product plant of a genus *Salacia* is not less than 0.5 mg/kg/day.

[4] The agent for suppressing the number of intestinal bacteria according to any one of [1] to [3], which is used for prevention or treatment of a gastrointestinal symptom.

[5] The agent for suppressing the number of intestinal bacteria according to [4], wherein the gastrointestinal symptom is a symptom of at least one disease selected from the group consisting of functional dyspepsia, irritable bowel syndrome, inflammatory bowel diseases, Crohn's disease, and ulcerative colitis.

[6] A food for suppressing the number of intestinal bacteria which is selected from the group consisting of the families Lachnospiraceae, Ruminococcacea, Fusobacteriaceae, and Desulfovibrionaceae, which contains the agent for suppressing the number of intestinal bacteria according to any one of [1] to [5].

[7] A pharmaceutical product for suppressing the number of intestinal bacteria which is selected from the group consisting of the families Lachnospiraceae, Ruminococcacea, Fusobacteriaceae, and Desulfovibrionaceae, which contains the agent for suppressing the number of intestinal bacteria according to any one of [1] to [5].

Further, according to the present invention, there is provided a method for suppressing the number of intestinal bacteria, the method comprising administering an extract and/or crushed product of a plant of the genus *Salacia* to a subject in need of suppression of the number of intestinal bacteria, wherein the intestinal bacterium is at least one which is selected from the group consisting of the families Lachnospiraceae, Ruminococcaceae, Fusobacteriaceae, and Desulfovibrionaceae.

Still further, according to the present invention, there is provided an extract and/or crushed product of plant of the genus *Salacia*, for use in the treatment of suppressing the number of intestinal bacteria, wherein the intestinal bacterium is at least one which is selected from the group consisting of the families Lachnospiraceae, Ruminococcaceae, Fusobacteriaceae, and Desulfovibrionaceae.

Yet further, according to the present invention, there is provided the use of an extract and/or crushed product of a plant of the genus *Salacia* for producing an agent for suppressing the number of intestinal bacteria, wherein the intestinal bacterium is at least one which is selected from the group consisting of the families Lachnospiraceae, Ruminococcaceae, Fusobacteriaceae, and Desulfovibrionaceae.

Yet further, according to the present invention, there is provided the use of an extract and/or crushed product of a plant of the genus *Salacia* for producing a food for suppressing the number of intestinal bacteria which are selected from the group consisting of the families Lachnospiraceae, Ruminococcaceae, Fusobacteriaceae, and Desulfovibrionaceae.

Yet further, according to the present invention, there is provided the use of an extract and/or crushed product of a plant of the genus *Salacia* for producing a pharmaceutical product for suppressing the number of intestinal bacteria which are selected from the group consisting of the families Lachnospiraceae, Ruminococcaceae, Fusobacteriaceae, and Desulfovibrionaceae.

Advantageous Effects of Invention

According to the present invention, it is possible to suppress the number of intestinal bacteria which is at least one selected from the group consisting of the families Lachnospiraceae, Ruminococcaceae, Fusobacteriaceae, and Desulfovibrionaceae by orally taking the agent for suppressing the number of intestinal bacteria, food or pharmaceutical product according to the present invention.

In addition, according to the present invention, the number of the above particular intestinal bacteria can be suppressed. Preferably, the number of the above particular intestinal bacteria can be reduced.

Further, according to the present invention, bowel diseases and/or symptoms thereof can be alleviated in subjects (e.g., mammals including humans and model animals) using the agent for suppressing the number of intestinal bacteria containing an extract and/or crushed product of a plant of the genus *Salacia*.

DESCRIPTION OF EMBODIMENTS

Embodiments of the present invention are described below.

[Agent for Suppressing the Number of Intestinal Bacteria]

The agent for suppressing the number of intestinal bacteria of the present invention is an agent for suppressing the number of intestinal bacteria containing an extract and/or crushed product of a plant of the genus *Salacia*, wherein the intestinal bacterium is at least one which is selected from the group consisting of the families Lachnospiraceae, Ruminococcaceae, Fusobacteriaceae, and Desulfovibrionaceae.

Although bacteria of the families Lachnospiraceae, Ruminococcaceae, Fusobacteriaceae, and Desulfovibrionaceae are associated with particular diseases, it has not been reported that the number of such intestinal bacterium can be reduced by using an extract and/or crushed product of a plant of the genus *Salacia*, which was first found by the present inventors. In the present invention, this finding suggests that an extract and/or crushed product of a plant of the genus *Salacia* is effective for prevention or treatment of diseases associated with the aforementioned bacteria. According to the present invention, new applications of an extract and/or crushed product of a plant of the genus *Salacia* are provided.

<Extract and/or Crushed Product of a Plant of the Genus *Salacia*>

Plants of the genus *Salacia* are plants of the family Hippocrateaceae that grow wild mainly in Sri Lanka, India, and the Southeast Asian region. Specific examples thereof include at least one plant selected from the group consisting of *Salacia reticulata*, *Salacia oblonga*, *Salacia prinoides*, *Salacia chinensis*, *Salacia latifolia*, *Salacia burunoniana*, *Salacia grandiflora*, and *Salacia macrosperma*. A plant of the genus *Salacia* is preferably at least one plant selected from the group consisting of *Salacia reticulata*, *Salacia oblonga*, and *Salacia chinensis*.

The expression "extract and/or crushed product of a plant of the genus *Salacia*" used herein refers to a crushed product and/or extract of edible parts such as roots, stems, leaves, flowers, and fruits of a plant of the genus *Salacia* or a dried product of the crushed product and/or extract. The term "dried product" used herein may refer to a dry powder (extract powder). When a extract and/or crushed product of the plant of the genus *Salacia* is prepared, at least one part of a plant of the genus *Salacia* may be mixed for use. As an extract of a plant of the genus *Salacia*, an extract powder obtained by drying an extract of a part selected from roots and stems is more preferably used.

Preferably, such dry powder (extract powder) can be obtained by extracting, for example, edible parts of a plant of the genus *Salacia* with a solvent and drying the obtained extract. A solvent used for extraction may be water, alcohol, ketone, or the like or a mixed solvent of two or more thereof. Examples of alcohol include methanol and ethanol. Ethanol is preferable. Preferable examples of ketone include acetone, methyl ethyl ketone, and cyclohexane.

Among the above examples, water, alcohol, a mixed solvent of water and alcohol, or a mixed solvent of water and ketone is preferable. Water, alcohol, or a mixed solvent of water and alcohol is more preferable. Hot water at 50° C. to 98° C., ethanol, or a mixed solvent of water and ethanol is further preferable.

The alcohol content in a mixed solvent of water and alcohol is preferably 30% by mass to 90% by mass and more preferably 40% by mass to 70% by mass. A drying method for drying an extract to obtain a dry powder (extract powder) is not particularly limited. A conventionally known drying method such as spray drying or lyophilization can be used. It is also possible to obtain a dry powder using a conventionally known excipient such as a sugar (e.g., dextrin). In order to obtain a dry powder with increased activity, it is preferable to obtain a dry powder by directly drying (e.g., spray drying) an extract.

<Intestinal Bacteria>

Regarding the agent for suppressing the number of intestinal bacteria of the present invention, the intestinal bacterium is at least one bacterium which are selected from the group consisting of the families Lachnospiraceae, Ruminococcaceae, Fusobacteriaceae, and Desulfovibrionaceae.

The word "intestinal" used herein means "gastrointestinal" in an animal (preferably mammals including humans) wherein the gastrointestinal tracts have the resident flora containing bacteria of the families Lachnospiraceae, Ruminococcaceae, Fusobacteriaceae and Desulfovibrionaceae for digestion and absorption. Such gastrointestinal tract is preferably, but is not limited to, the small or large intestine of humans, and therefore, it may be the gastrointestinal tract of a no-human animal (e.g., dog, horse, cattle, pig, mouse, rat, or monkey).

Examples of bacteria of the family Lachnospiraceae include bacteria of the genera *Blautia, Anaerostipes, Coprococcus, Dorea, Roseburia*, and *Lachnospira*.

Examples of bacteria of the family Ruminococcaceae include bacteria of the genera *Ruminococcus, Faecalibacterium, Oscillospira*, and *Anaerotruncus*.

Examples of bacteria of the family Fusobacteriaceae include bacteria of the genus *Fusobacterium*.

Examples of bacteria of the family Desulfovibrionaceae include bacteria of the genera *Desulfovibrio* and *Bilophila*.

It is possible to confirm by the method described below whether or not the number of at least one bacterium which are selected from the group consisting of the families Lachnospiraceae, Ruminococcaceae, Fusobacteriaceae, and Desulfovibrionaceae can be suppressed by using the agent for suppressing the number of intestinal bacteria of the present invention.

A test subject is instructed to ingest a predetermined amount of the agent for suppressing the number of intestinal bacteria of the present invention for a certain period of time. Fecal sampling is conducted before and after the period of ingestion. DNA is extracted from the sampled feces. A sequence library is prepared using the obtained DNA. Sequencing is performed using a next-generation sequencer (MiSeq; Illumina, Inc.). Highly analogous data are divided into groups (i.e., operation taxonomic units (OTUs)) in order to estimate a phylogenetic system. The number of sequence data belonging to each phylogenetic group is counted for comparison of data obtained before and after the ingestion period. However, as the abundance largely differs among bacteria, the initial value is set to 100. As a result of comparison of the number of bacteria before and after the ingestion period, if the value obtained after the ingestion period is less than 100, it is determined that the number of certain bacteria can be suppressed.

<α-Glucosidase Inhibitory Activity>

The agent for suppressing the number of intestinal bacteria of the present invention contains an extract and/or crushed product of a plant of the genus *Salacia*. Note that it may or may not have α-glucosidase inhibitory activity.

The 50% inhibitory concentration ($IC_{50}$) of sucrase, which is used as an index of α-glucosidase inhibitory activity, can be determined by the method described below.

[Experimental Method 1] Determination of $IC_{50}$ of Sucrase

Preparation of Sample Solutions:

A sample is weighed (2 mg) and placed in a tube. Water (2 mL) is added thereto to suspend the sample sufficiently. Thus, a sample solution at a concentration of 1 mg/mL is prepared. The sample solution is diluted with water to prepare sample solutions at concentrations of 0, 50, 100, 250, and 500 μg/mL.

Preparation of a Substrate Solution:

Sucrose is dissolved in a 0.2 mol/L maleic acid buffer (pH 6.0) so as to result in a sucrose concentration of 100 mmol/L. Thus, a substrate solution is prepared.

Preparation of a Crude Enzyme Liquid:

Intestinal acetone powder rat (1 g, SIGMA) is suspended in physiological saline (10 mL), followed by centrifugation (3,000 rpm, 4° C., 5 minutes). The resulting supernatant is separated to obtain a crude enzyme solution.

The substrate solution (400 μL) is added to each of the sample solutions with the above concentrations (500 μL), followed by prewarming in water bath at 37° C. for 5 minutes. The crude enzyme solution (100 μL) is added thereto to allow a reaction to take place at 37° C. for 60 minutes. After the completion of reaction, each solution is heated at 95° C. for 2 minutes so as to deactivate the enzyme to terminate the reaction. The glucose concentration of each obtained product is quantitatively determined using a commercially available kit by a mutarotase/glucose oxidase method (Glucose CII Test Wako, Wako Pure Chemical Industries, Ltd.).

Preparation of a Blank:

The substrate solution (200 μL) and the crude enzyme solution (50 μL) are added to each sample solution (250 μL) with the relevant concentration, and the mixture is immediately heated at 95° C. for 2 minutes so as to deactivate the enzyme by heat to obtain blank data. A calibration curve is created based on the obtained values so as to determine the concentration at which enzymatic activity is inhibited by 50% ($IC_{50}$).

<Other Components>

The agent for suppressing the number of intestinal bacteria of the present invention may contain other components, in addition to an extract and/or crushed product of a plant of the genus *Salacia*. Examples of other components include, but are not limited to, lactic acid bacteria, mineral yeast, flavonoid, polyphenol, and other orally ingestible substances having an immunostimulatory action. Specific examples of the other components include components described in Japanese Unexamined Patent Publication No. 2015-127340 (paragraph nos. 0023 to 0038).

The agent for suppressing the number of intestinal bacteria of the present invention may further contain an orally ingestible component, such as at least one which is selected from the group consisting of vitamins, vitamin-like substances, proteins, amino acids, fat and oil, organic acids, carbohydrates, plant-derived material, animal-derived material, microorganisms, food additives, and additives for pharmaceutical products according to need.

<Formulation>

The agent for suppressing the number of intestinal bacteria of the present invention can be prepared using at least one additive selected from the group consisting of a variety of pharmaceutically or food hygienically acceptable carriers such as excipients, lubricants, stabilizers, dispersions, binders, diluents, flavoring agents, sweeteners, corrigents, and coloring agents. Preferably, it can be prepared as an orally administered agent.

The form of the agent for suppressing the number of intestinal bacteria of the present invention is not particularly limited as long as the effects of the present invention can be obtained. Examples thereof include tablets, pills, granules, fine granules, masticatories, capsules (filled hard or soft capsules), liquid agents, chewable agents, and food products described below (including beverage products).

The agent for suppressing the number of intestinal bacteria of the present invention can be prepared in the above form by a conventional method known to those skilled in the art.

Tablets, pills, and granules of the agent for suppressing the number of intestinal bacteria of the present invention can be prepared with a conventionally known coating so as to obtain sugar-coated tablets, gelatin-coated tablets, enteric-coated agents, film-coated agents, or the like according to need. The tablets may be multi-coated tablets such as double-coated tablets.

According to the present invention, in order to prevent time-dependent discoloration of an extract and/or crushed product of a plant of the genus *Salacia*, it is preferable to add, as a desiccant, calcium carbonate and/or silicon dioxide (preferably silicon dioxide particle)). If the agent for suppressing the number of intestinal bacteria of the present invention is in the form of tablets or capsules, the agent for suppressing the number of intestinal bacteria of the present invention preferably contains calcium carbonate and/or silicon dioxide in an amount that accounts for 1% or more of the mass of tablets or capsules. The contents of calcium carbonate and silicon dioxide may be 1% by mass or more. The total content of calcium carbonate and silicon dioxide may be 1% by mass or more. For edible use, the upper limit of the content of calcium carbonate is 2.5% by mass and the upper limit of the content of silicon dioxide is 2.0% by mass in accordance with the Food Sanitation Act. Therefore, when the agent for suppressing the number of intestinal bacteria of the present invention is provided as a food, the contents of calcium carbonate and silicon dioxide are preferably 2.5% by mass or less and 2.0% by mass or less, respectively.

The agent for suppressing the number of intestinal bacteria of the present invention may be mixed with low hygroscopic material, a hygroscopic agent, an antioxidant, and the like, which can be used as foods or food additives. Preferable examples of low hygroscopic material that can be used include cellulose, crystalline cellulose, powdered cellulose, fine crystalline cellulose, lactose, oligosaccharide, sugar alcohol, trehalose, magnesium stearate, calcium stearate, and sucrose fatty acid ester. Examples of a hygroscopic agent that can be used include silicates, magnesium carbonate, ferrocyanide, and polysaccharides. More preferable examples of low hygroscopic material that can be used include crystalline cellulose, fine crystalline cellulose, lactose, and sucrose fatty acid ester. Examples of an antioxidant that can be used include ascorbic acid and sodium ascorbate.

The agent for suppressing the number of intestinal bacteria of the present invention may further contain a compound that is necessary to form the agent into a powder, solid agent, or liquid agent. Examples of such compound include erythritol, maltitol, hydroxypropylcellulose, kaolin, and talc.

<Usage>

The agent for suppressing the number of intestinal bacteria of the present invention can be orally administered to mammals (e.g., humans) as subjects.

In another aspect of the present invention, there is provided a method for suppressing the number of intestinal bacteria, the method comprising administering an extract and/or crushed product of a plant of the genus *Salacia* to a subject in need of suppression of the number of intestinal bacteria, wherein the intestinal bacterium is at least one which is selected from the group consisting of the families Lachnospiraceae, Ruminococcaceae, Fusobacteriaceae, and Desulfovibrionaceae.

When the agent for suppressing the number of intestinal bacteria of the present invention is administered to, for example, a human, the daily intake or dose of an extract and/or crushed product of a plant of the genus *Salacia* is preferably 0.1 mg/kg/day or more, more preferably 0.5 mg/kg/day or more, and further preferably 1.0 mg/kg/day or more, and yet further preferably 2.0 mg/kg/day or more, yet further preferably 4.0 mg/kg/day or more. The upper limit of the daily intake or dose of an extract and/or crushed product of a plant of the genus *Salacia* is not particularly limited. It is generally 100 mg/kg/day or less, and preferably 50 mg/kg/day or less.

The amount of an extract and/or crushed product of a plant of the genus *Salacia* contained in the agent for suppressing the number of intestinal bacteria of the present invention can be appropriately determined. For instance, when tablets are administered at a daily intake of 3 tablets, such tablets are prepared in a manner such that each tablet preferably contains one-third of the daily intake.

The agent for suppressing the number of intestinal bacteria of the present invention can be used for prevention or treatment of gastrointestinal symptoms.

It is known that bacteria of the family Lachnospiraceae are associated with diabetes (e.g., WO2013/146319). It is known that bacteria of the families Ruminococcaceae, Fusobacteriaceae, and Desulfovibrionaceae are associated with gastrointestinal diseases and cancer (e.g., large bowel cancer) (e.g., Ohkusa T. *Fusobacterium*, Ulcerative Colitis and Colorectal Cancer, Journal of Intestinal Microbiology, 2013; 27:169-79, Fox J, Dewhirst F, Fraser G, Paster B, Shames B, Murphy J. Intracellular Campylobacter-like organism from ferrets and hamsters with proliferative bowel disease is a *Desulfovibrio* sp. Journal of clinical microbiology, 1994; 32(5):1229-37).

Ingestion of the agent for suppressing the number of intestinal bacteria of the present invention enables suppression of the number of bacteria of the families Lachnospiraceae, Ruminococcaceae, Fusobacteriaceae, and Desulfovibrionaceae, which are causative bacteria of diseases accompanied by gastrointestinal symptoms. Accordingly, gastrointestinal symptoms can be prevented or treated.

Examples of diseases accompanied by gastrointestinal symptoms include diabetes, gastrointestinal diseases, and cancer (e.g., large bowel cancer). Examples of gastrointestinal symptoms include, but are not limited to, symptoms of at least one disease selected from the group consisting of functional dyspepsia (FD), irritable bowel syndrome (IBS), inflammatory bowel disease (IBD), Crohn's disease (CD), and ulcerative colitis (UC).

The agent for suppressing the number of intestinal bacteria of the present invention is expected to be effective for prevention or treatment of the above diseases. Since the gastrointestinal tract is an organ that excretes foreign substances, if the function of the gastrointestinal tract is impaired due to deterioration of the intestinal flora, it could cause the retention of substances harmful for the body (e.g., putrefactive products), thereby inducing a feeling of abdominal bloating, a feeling of abdominal illness, a feeling of abdominal fatigue, and the like. In addition, there is concern that in vivo reabsorption of retaining substances harmful for the body might affect various organs such as liver, kidney, and pancreas, thereby causing liver damage, carcinogenesis, and the development of diseases such as arteriosclerosis, and it might further cause deterioration of skin conditions, accumulated fatigue, poor health, deterioration of sleeping conditions, and the like in daily living. It is expected to be possible to reduce body weight and body fat and ameliorate abdominal symptoms such as constipation and diarrhea by ingesting the agent for suppressing the number of intestinal bacteria of the present invention. Surprisingly, it is also expected to be possible to improve feelings in daily living (i.e., the improvement of quality of life (QOL)) by ingesting the agent for suppressing the number of intestinal bacteria of the present invention. The agent for suppressing the number of intestinal bacteria of the present invention is safe and has few side effects in long-term use.

<Food and Pharmaceutical Product>

The form of the agent for suppressing the number of intestinal bacteria of the present invention is not particularly limited. For example, it may be a food (such as a beverage product or supplement), a food ingredient, a quasi-drug, a pharmaceutical product, a pharmaceutical product ingredient, or a quasi-drug ingredient.

According to the present invention, the following are provided: a food for suppressing the number of intestinal bacteria which are selected from the group consisting of the families Lachnospiraceae, Ruminococcaceae, Fusobacteriaceae, and Desulfovibrionaceae, which contains the agent for suppressing the number of intestinal bacteria of the present invention; and a pharmaceutical product for suppressing the number of intestinal bacteria which are selected from the group consisting of the families Lachnospiraceae, Ruminococcaceae, Fusobacteriaceae, and Desulfovibrionaceae, which contains the agent for suppressing the number of intestinal bacteria of the present invention.

The pharmaceutical product of the present invention may be provided as a pharmaceutical product containing the agent for suppressing the number of intestinal bacteria of the present invention in any form described above.

In another embodiment of the pharmaceutical product of the present invention, a pharmaceutical product which further contains the following compound of structural formula 1 (hereinafter referred to as a "compound of structural formula 1") is preferable.

Structural formula 1

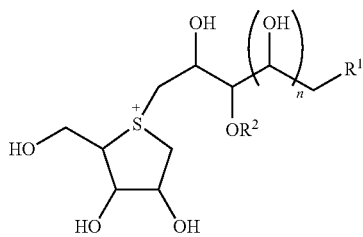

In structural formula 1, n denotes an integer of 0 to 4, $R^1$ denotes a hydrogen atom, —OH, —(CH(OH))$_m$—CH$_2$OH (m denotes an integer of 0 to 2), C1-C16 alkyl, or C3-C6 cycloalkyl.

$R^2$ denotes a hydrogen atom, —SO$_3^-$, C1-C16 alkyl, or C3-C6 cycloalkyl.

In addition, the above C1-C16 alkyl or C3-C6 cycloalkyl includes a compound substituted with a substituent such as a halogen atom (e.g., a fluorine atom or a chlorine atom), hydroxy, amino, or nitro.

In structural formula 1, an anion serving as a counter ion of a sulfonium ion is a conjugate base ion of Brønsted acid.

Specific examples of a conjugate base ion of Brønsted acid include, but are not limited to, halogen ions (e.g., F$^-$, Cl$^-$, and Br$^-$); sulfonate ions (e.g., CH$_3$SO$_3^-$, C$_2$H$_5$SO$_3^-$, CF$_3$SO$_3^-$, and p-CH$_3$C$_6$H$_4$SO$_3^-$); alkyl sulfate ions (e.g., CH$_3$OSO$_3^-$, C$_2$H$_5$OSO$_3^-$, CF$_3$OSO$_3^-$, and p-CH$_3$C$_6$H$_5$OSO$_3^-$); carboxylate ions (e.g., HCOO$^-$, CH$_3$COO$^-$, CF$_3$COO$^-$, and C$_6$H$_5$COO$^-$); phosphate ion, monohydrogenphosphate ion, dihydrogenphosphate ion; ClO$_4^-$ ion; and conjugate bases of compounds comprising Lewis acid and hydrogen halide (e.g., BF$_4^-$ and PF$_6^-$). Preferably, a conjugate base ion of Brønsted acid is Cl$^-$ or BF$_4^-$.

The intake or dose of the compound of structural formula 1 may vary depending on the subject of administration, disease, symptoms, dosage form, administration route, and other factors. However, for example, the daily intake or dose of the compound of structural formula 1 to be orally administered to a human (body weight: about 60 kg) is from 1 mg to 1 g. It is also possible to administer or ingest such intake or dose in a single dose or several divided doses.

Examples of the food of the present invention include health foods (e.g., tablets, granules, capsules, and powders), tonic drinks, and beverage products.

The form of the food of the present invention is not particularly limited. The food of the present invention may be in a variety of forms as long as it can be supplied in the body mainly via the oral route. For example, the food of the present invention can be provided in the following forms: powdered foods, granulated foods, sheet-type foods, bottled foods, canned foods, retort foods, capsulated foods, tablet foods, liquid foods, and tonic drinks. The food of the present invention can be used as a health food, a functional food, a dietary supplement, a food for specified health use, or the like. In a case in which the food of the present invention is a functional food, it is preferably provided as a tablet food, a granulated food, or a capsulated dietary supplement as well as a general food/beverage such as a tonic drink, a revitalizer, a discretionary beverage product, or a frozen dessert.

The food of the present invention may contain generally used food components according to need, in addition to the agent for suppressing the number of intestinal bacteria of the present invention. Examples of components that can be used for the food of the present invention include coloring agents, preservatives, thickening and stabilizing agents, antioxidants, color formers, bleaching agents, fungicides, gum bases, bittering agents, enzymes, brighteners, acidulants, seasonings, emulsifiers, fortifier dietary supplements, additives for food production (excipients), flavoring agents, spice extracts, and pH adjusters.

As in the case of the composition mentioned above, pH of the food of the present invention is preferably 8.0 or less, more preferably 7.0 or less, and further preferably 3.0 to 6.0 in consideration of the improvement of stability of salacinol. Any pH adjuster can be used herein for adjustment of pH of food as long as it is conventionally used in the field of foods.

Examples of pH adjusters that can be used for foods include: organic acids such as gluconic acid, L-tartrate, malic acid, lactic acid, adipic acid, succinic acid, acetic acid, fumaric acid, phytic acid, and derivatives thereof; and inorganic acids such as baking soda (sodium hydrogen carbonate), sodium carbonate, sodium hydroxide, calcium hydroxide, disodium hydrogen phosphate, sodium dihydrogen phosphate, dipotassium hydrogen phosphate, potassium dihydrogen phosphate, and potassium carbonate.

Such organic acids may be in the form of salts such as sodium salts, potassium salts, and magnesium salts. The above pH adjusters may be used alone or in combination of two or more thereof.

Examples of other components that can be used for foods include milk proteins, soybean proteins, egg albumin proteins, or egg albumen oligopeptides which are decomposed products of the above, soybean hydrolyzates, and a mixture of amino acids.

In addition, the food of the present invention can be in the form of a processed product such as a natural liquid food, a semi-digested nutritional food and a nutritional food, a tonic agent, a capsulated agent, or an enteral nutrient, wherein sugars, fat, trace elements, vitamins, emulsifiers, flavoring agents, or the like are mixed.

In a case in which the food of the present invention is prepared in the form of a tonic agent, it is possible to add nutritional additives (e.g., amino acids, vitamins, and minerals), sweeteners, seasonings, flavoring agents, food coloring agents, and the like in order to improve nutritional balance and the flavor during ingestion.

When the agent for suppressing the number of intestinal bacteria of the present invention is used for foods, the content thereof can be appropriately determined depending on the intended use. In consideration of optimization of efficacy of an extract and/or crushed product of a plant of the genus *Salacia*, the content of an extract and/or crushed product of a plant of the genus *Salacia* with respect to the total amount of the food of the present invention is preferably 1% by mass to 60% by mass and more preferably 1% by mass to 40% by mass.

<Intended Use of the Extract and/or Crushed Product of a Plant of the Genus *Salacia*>

In one aspect of the present invention, there is provided an extract and/or crushed product of a plant of the genus *Salacia* for use in the treatment of suppressing the number of intestinal bacteria, wherein the intestinal bacterium is at least one which is selected from the group consisting of the families Lachnospiraceae, Ruminococcaceae, Fusobacteriaceae, and Desulfovibrionaceae. In another aspect of the present invention, there is provided the use of an extract and/or crushed product of a plant of the genus *Salacia* for producing an agent for suppressing the number of intestinal bacteria, wherein the intestinal bacterium is at least one which is selected from the group consisting of the families Lachnospiraceae, Ruminococcaceae, Fusobacteriaceae, and Desulfovibrionaceae. In yet another aspect of the present invention, there is provided the use of an extract and/or crushed product of a plant of the genus *Salacia* for producing a food or pharmaceutical product for suppressing the number of intestinal bacteria which are selected from the group consisting of the families Lachnospiraceae, Ruminococcaceae, Fusobacteriaceae, and Desulfovibrionaceae.

Preferable embodiments of the present invention are as per specified herein.

<Kit>

It is also possible to provide a kit including a combination of the agent for suppressing the number of intestinal bacteria of the present invention and a member and/or reagent for intestinal bacterial testing.

Examples of a member for intestinal bacterial testing include a container for fecal sampling (which may contain a solution for sample preservation for intestinal bacterial testing), a sheet, and a sampling tool.

Examples of a reagent for intestinal bacterial testing include a sample containing synthetic DNA fragments or primers having sequences specific to particular bacteria and a reagent for performing DNA amplification reaction by PCR (polymerase chain reaction).

A subject, who has been found to be in need of suppression of the number of intestinal bacteria which are selected from the group consisting of the families Lachnospiraceae, Ruminococcaceae, Fusobacteriaceae, and Desulfovibrionaceae as a result of intestinal bacterial testing with the use of the member and/or reagent, is allowed to ingest the agent for suppressing the number of intestinal bacteria of the present invention.

EXAMPLES

The present invention will be described in more detail with reference to the following examples. However, these examples are not intended to limit the scope of the present invention. The term "Tris" is used herein to indicate an abbreviation for Tris(hydroxymethyl)aminomethane. Also, the term "EDTA" is used herein to indicate an abbreviation for ethylenediaminetetraacetic acid.

Example 1

Roots and stems of *Salacia reticulata* and *Salacia oblonga* were crushed and mixed in equal weight, followed by extraction with hot water at 98° C. The resulting solution was spray-dried. Thus, an extract powder of a plant of the genus *Salacia* was obtained. Tablets (250 mg/tablet) were produced using the obtained extract powder based on the mass ratio shown in Table 1.

TABLE 1

| Raw material name | Mass ratio (% by mass) |
|---|---|
| Extract powder of plants of the genus *Salacia* | 24.0 |
| Crystalline cellulose | 69.1 |
| Sucrose fatty acid ester | 3.0 |
| Calcium carbonate | 2.4 |
| silicon dioxide particle | 1.5 |

Example 2 (Human Intestinal Bacteria)

Male adults (25 individuals) were instructed to ingest, as a test meal, 1 g of tablets containing an extract powder of a plant of the genus *Salacia* described in Example 1 on a daily basis for 4 weeks. Fecal sampling was conducted before and after the ingestion period using fecal sampling kits (TechnoSuruga Laboratory Co., Ltd., Shizuoka, Japan). The obtained fecal samples were suspended in GTC (guanidine thiocyanate) Buffer (100 mM Tris-HCl [pH 9.0], 40 mM Tris-EDTA [pH 8.0], 4M Guanidine Thiocyanate). Feces in each suspension was crushed using zirconia beads. DNA was extracted from 100 µl of each suspension using an automated nucleic acid isolation system (Precision System Science, Chiba, Japan). Samples for a sequence library were prepared using the obtained DNA and Nextera™ DNA sample preparation kits (Illumina, Inc.). In addition, an index sequence was added to each sample (in accordance with the protocol of the kits), thereby making it possible to identify samples. Sequencing was performed using the prepared sequence library and a next-generation sequencer (MiSeq; Illumina, Inc.). The obtained data were subjected to nucleotide sequence quality check for filtering low-quality data. Among data that had cleared the requirement of quality check, highly analogous data were divided into groups (i.e., operation taxonomic units (OTUs)). Each OTU was subjected to homology search on the 16S rRNA gene database in order to estimate a phylogenetic system. The number of sequence data belonging to each phylogenetic group was counted for comparison of data obtained before and after the ingestion period. However, as the abundance largely differs among bacteria, the initial value was set to 100. As a result of comparison of the number of bacteria before and after the ingestion period, when the value obtained after the ingestion period was less than 100, it was determined that a certain number of bacteria could be suppressed. Table 2 shows the measurement results.

TABLE 2

| | Before ingestion | After ingestion |
|---|---|---|
| The family Lachnospiraceae | 100 | 67.3 |
| The family Ruminococcaceae | 100 | 36.3 |
| The genus *Fusobacterium* of the family Fusobacteriaceae | 100 | 2.9 |
| The genus *Desulfovibrio* of the family Desulfovibrionaceae | 100 | 7.5 |

As shown in Table 2, as a result of ingestion of the extract powder of a plant of the genus *Salacia*, the amount of DNA of each bacterium (the number of bacteria) decreased. The above bacteria have been confirmed to be involved in the development or aggravation of diabetes and bowel diseases. It is expected to be possible to prevent the development of diseases or alleviate symptoms of the diseases by reducing the above bacteria.

The bacteria of the family Lachnospiraceae in Example 2 contained bacteria of the genera *Blautia*, *Anaerostipes*, *Coprococcus*, *Dorea*, *Roseburia*, and *Lachnospira*. The bacteria of the family Ruminococcaceae in Example 2 contained the genera *Ruminococcus*, *Faecalibacterium*, and *Oscillospira*.

Example 3 (Ulcerative Colitis Model)

Eight-week-old C57BL/6 (C57 black 6) mice (female) were divided into 5 groups (5 mice each). The doses of the extract powder of a plant of the genus *Salacia* administered to the respective groups were as follows: (1) 0.0 mg/kg/day; (2) 0.5 mg/kg/day; (3) 5.0 mg/kg/day; (4) 50.0 mg/kg/day; and (5) 0.0 mg/kg/day (control). Each mouse was forcibly fed with the extract powder of a plant of the genus *Salacia* suspended in physiological saline via oral administration. One week later, the groups (1) to (4) were allowed to freely drink dextran sulfate sodium (DSS) (3% by mass), thereby inducing bowel inflammation (ulcerative colitis model). In addition, the extract powder of a plant of the genus *Salacia* was continuously administered during DSS administration. On day 6 after the start of DSS administration, the severity of inflammation was evaluated based on the disease activity index (DAI). The disease activity index (DAI) is used for evaluation of the severity of inflammation based on the scores of body weight decrease and diarrhea.

Scoring was carried out based on the criteria described below (reference: Yoshihara K, Yajima T, Kubo C, Yoshikai Y. Role of interleukin 15 in colitis induced by dextran sulphate sodium in mice. Gut. 2006; 55(3): 334-41).
No body weight decrease: 0
body weight decrease by 1% to 5%: 1
body weight decrease by 5% to 10%: 2
body weight decrease by 10% to 15%: 3; and
body weight decrease by 15% or more: 4
Normal feces: 0
soft feces: 1 to 3
diarrhea: 4

The extract powder of a plant of the genus *Salacia* was considered to inhibit inflammation in the living body and alleviate inflammatory symptoms by reducing the inflammatory cytokine level in blood.

TABLE 3

| Dosing group | DAI |
| --- | --- |
| (1) 0.0 mg/kg | 7.5 |
| (2) 0.5 mg/kg | 5.2 |
| (3) 5.0 mg/kg | 4.0 |
| (4) 50.0 mg/kg | 3.3 |
| (5) Control | 0.3 |

As shown in Table 3, it was confirmed that the administration of the extract powder of a plant of the genus *Salacia* enables alleviation or inhibition of inflammation.

Example 4 (Questionnaire Survey)

Male adults (10 individuals) were instructed to ingest, as a test meal, 1 g (4 tablets) of extract powder of a plant of the genus *Salacia* described in Example 1 on a daily basis. Then, a questionnaire survey on subjective symptoms was conducted. They were asked to answer for each test item by selecting an option that was most applicable to one's own conditions from the following: 1: "completely not applicable;" 2: "almost not applicable;" 3: "probably not applicable;" 4: "probably applicable;" 5: "almost applicable;" and 6: "completely applicable." The value before ingestion was determined to be 100% so as to obtain the rate of change after ingestion. An increase in the value corresponds to an increase in the severity of symptom while a decrease in the value indicates improvement. The p value was less than 0.05 for each test item below (p<0.05) (p represents the p value (probability)).

TABLE 4

| Test item | Before ingestion | After ingestion |
| --- | --- | --- |
| Having physical fatigue | 4.7 ± 0.7 | 2.8 ± 0.9 |
| Suffering from insomnia | 3.4 ± 1.3 | 2.2 ± 0.8 |
| Feeling fatigue even after taking a long rest | 4.6 ± 0.8 | 3.1 ± 0.7 |
| Laughing less often than before | 3.4 ± 1.4 | 2.5 ± 1.4 |
| Often having a swelling or an uncomfortable feeling on the throat | 3.3 ± 1.3 | 2.1 ± 0.9 |
| Having spots and pimples | 3.7 ± 0.9 | 2.7 ± 1.5 |
| Having a feeling of incomplete evacuation | 2.9 ± 1.4 | 1.9 ± 1.0 |
| Having a feeling of abdominal bloating | 3.0 ± 0.9 | 1.8 ± 0.8 |
| Having a heavy abdominal feeling | 2.8 ± 1.1 | 1.8 ± 0.8 |

As shown in Table 4, it was revealed that it is possible to improve physical fatigue, depression, abdominal symptoms, and the like by ingesting an extract powder of a plant of the genus *Salacia* to an extent greater than expected.

The invention claimed is:

1. A method for suppressing the number of intestinal bacteria, the method comprising determining the number of intestinal bacteria in a fecal sample obtained from a subject, identifying a subject in need of suppression of the number of intestinal bacteria, and administering an extract and/or crushed product of a plant of the genus *Salacia* to the subject in need of suppression of the number of intestinal bacteria, wherein the plant of the genus *Salacia* is at least one plant selected from the group consisting of *Salacia recticulata*, *Salacia oblonga* and *Salacia chinensis*, and the intestinal bacterium is at least one which is selected from the group consisting of the genera *Blautia*, *Anaerostipes*, *Coprococcus*, *Dorea*, *Roseburia*, *Lachnospira*, *Ruminococcus*, *Faecalibacterium*, *Oscillospira*, *Anaerotruncus*, *Fusobacterium*, *Desulfovibrio*, and *Bilophila*.

2. The method according to claim 1, wherein the intestinal bacterium is at least one which is selected from the group consisting of the the genus *Lachnospira*, the genus *Ruminococcus*, the genus *Fusobacterium*, and the genus *Desulfovibrio*.

3. The method according to claim 1, wherein the intake or dose of the extract and/or crushed product plant of a genus *Salacia* is not less than 0.5 mg/kg/day.

4. The method according to claim 1, which is used for prevention or treatment of a gastrointestinal symptom.

5. The method according to claim 4, wherein the gastrointestinal symptom is a symptom of at least one disease selected from the group consisting of functional dyspepsia, irritable bowel syndrome, inflammatory bowel diseases, Crohn's disease, and ulcerative colitis.

* * * * *